United States Patent [19]
Bass

[11] Patent Number: 5,993,841
[45] Date of Patent: Nov. 30, 1999

[54] PHARMACEUTICAL COMPOSITION AND METHODS FOR USING IT

[76] Inventor: James S. Bass, 12591 McGregor Blvd., Fort Meyers, Fla. 33919

[21] Appl. No.: 09/084,424

[22] Filed: May 27, 1998

Related U.S. Application Data

[63] Continuation-in-part of application No. 09/031,067, Feb. 26, 1998, which is a continuation-in-part of application No. 08/812,410, Mar. 6, 1997, Pat. No. 5,753,247.

[51] Int. Cl.⁶ .............................. A01N 25/00; A61K 7/00; A61K 31/70; A61K 31/56; A61K 31/545; A61K 31/135

[52] U.S. Cl. ........................ 424/404; 424/400; 424/401; 424/405; 514/39; 514/169; 514/170; 514/200; 514/653

[58] Field of Search ...................................... 424/400, 401, 424/404, 405; 514/39, 169, 170, 200, 653

[56] References Cited

U.S. PATENT DOCUMENTS

| | | | |
|---|---|---|---|
| 3,764,672 | 10/1973 | Argoudelis et al. | 424/181 |
| 4,226,850 | 10/1980 | Packman et al. | 424/47 |
| 4,568,343 | 2/1986 | Leeper et al. | 424/28 |

*Primary Examiner*—Shelley A. Dodson
*Attorney, Agent, or Firm*—Armstrong, Westerman, Hattori, McLeland & Naughton

[57] ABSTRACT

Disclosed is a method of treating problems or disorders of the human nervous system or a method of imparting an anaesthetic effect, by applying to a patient in need of such treatment a pharmaceutical composition adapted for topical application to human skin, comprising (A) as an effective ingredient, a mixture comprising
   (1) an antibiotic medication;
   (2) an antihistamine; and
(B) a physiologically acceptable carrier.

14 Claims, No Drawings

PHARMACEUTICAL COMPOSITION AND METHODS FOR USING IT

This is a Continuation-in-Part of application Ser. No. 09/031,067 filed Feb. 26, 1998 now allowed which is a Continuation-in-Part of Ser. No. 08/812,410 filed Mar. 6, 1997 now U.S. Pat. No. 5,753,247.

BACKGROUND OF THE INVENTION

The present invention is related to a topical composition which may be applied to skin for the purpose of treating problems or disorders of the nervous system in human patients and for imparting an anaesthetizing effect to a human patient.

Many compositions for treating problems or disorders of the nervous system and anaesthetic compositions are known in the art. But commonly their effectiveness is quite limited. It appears in most instances that the human body's own immune system actually defends the infected area of the body, thereby reducing the amount of composition which passes through the barrier of the immune system and reach the infection. By reducing the free transfer of the disease from the affected area to the healthy areas, the body prevents or reduces the spread of the disease. But this function has the drawback of impeding the transfer of composition to affected areas where they may perform their intended function.

The present inventor has found that by suppressing the immune system, a freer transfer of effective agent can be achieved; the more the immune system is suppressed, the more effective the agent becomes.

Accordingly, an object of the present invention is to provide a composition which may be applied to human skin where it will successfully address problems or disorders of the nervous system in human patients, without causing adverse side effects.

A further object of the present invention is to provide a composition which may be applied to the skin of a human patient, to impart an anaesthetisizing effect to that patient.

These and other objects are achieved by the present invention.

SUMMARY OF THE INVENTION

The present invention is a composition intended for the topical application to human skin, comprising
  (1) an antibiotic medication such as penicillin VK (Rugby), doxycycline (Rugby) or erythrocin (Abbott Laboratories); and
  (2) an antihistamine such as bromohenivamine (Schein), Chlorpromazine (Schein), diphenylhydramine hydrochloride (Parke-Davis), chlorpheniramine malate, chlorpromazine malate, and bromopheniramine.

Certain embodiments of the invention may also contain (3) an antiinflammatory medication such as aspirin (Goldline), hydrocortisone cream (Rugby), hydrocortisone powder (Parma-Tek Inc.) and hydrocortisone acetate injectable (Merck Sharp & Dohme), and/or (4) a bactericide combination of neomycin/bactracine/polymyxin B sulfate.

The inventor has surprisingly found that this combination of ingredients produces remarkable effects in treating problems or disorders of the nervous system in human patients, and impart an anaesthetisizing effect to that patient.

DETAILED DESCRIPTION OF THE INVENTION

The human body's immune system builds a multifunctional defensive barrier between an affected area and an unaffected area of the body. The more dangerous the immune system considers this affected area to be, the more pronounced the interference between the affected and unaffected areas becomes. The ability to provide medication to the affected area is also reduced in direct relation to the effectiveness of this interference.

The present applicant has found that by temporarily reducing the effectiveness of this defensive area, ordinary medications become very effective very quickly. The composition described Ad herein is intended to accomplish this result.

The composition described herein has been found to be effective in the treatment of nervous system conditions, such as Lou Gehrig's Disease.

Relative amounts of 30 to 70% by weight antihistamine to 70 to 30% by weight antibiotic/fungicide appear to be effective. Preferred relative amounts being 40 to 60% by weight antihistamine to 60 to 40% by weight antibiotic/fungicide, more preferred relative amounts being 45 to 55% by weight antihistamine to 55 to 45% by weight antibiotic/fungicide, and most preferred relative amounts being about 50 to about 50% by weight antihistamine to about 50 to about 50% by weight antibiotic/fungicide.

Although many combinations of types and brands of antihistamines and antibiotics and/or fungicides may be used effectively, antibiotics and fungicides which are known to work well with the particular infection to be treated, should be tried first.

It is desirable to mix the ingredients into a paste because a liquid is needed to carry the mixture of the invention into the affected area. The paste mixture should be kept moist to continue its effectiveness and to prevent undue drying of the mixture. If the paste mixture becomes unduly dry after application to the skin surface, it will tend to fall off the skin.

If the paste mixture is allowed to be dry on the skin, the addition of a cream may be helpful in holding the mixture together in place on the skin surface.

The composition of the present invention may be effectively held in place on the patient's skin by the use of a wax, such as the type of wax commonly used with braces for teeth.

The best results appear to be obtained with hydrocortisone cream. The antiinflammatory characteristics of the cortisone are believed to aid in the free flow of the antibiotics. Topical compositions according to the present invention, which contain cortisone cream, virtually eliminate infections within a few hours to a few days. Also, pain and bruising is reduced with the use of cortisone cream.

The components of the present invention may also be combined with blephamide as a carrier. Embodiments of the invention containing a sulfa drug as the antibiotic result in particularly fast recovery, as well as offering good anaesthetic effects. Especially good anaesthetic results are obtained when the sulfa drug is contained in Blephamide. In fact the present invention may also be characterized as a method for reducing pain through the application of the presently disclosed pharmaceutical composition when the antibiotic is a sulfa drug. Blephamide appears to be particularly effective in treating conditions on the eye lid or conditions effecting the surface of the skin such as burns.

Sulfa drugs are particularly effective in treating fungal infections, for instance fungal infections under the toes, in patients who also suffer from diabetes.

The healing process with the topical composition of the present invention appears to be different from that with conventional compositions. While the healing period with the present invention may be 50 to 75% longer than with such conventional compositions, the pain, swelling, and discoloration associated with the infected area are greatly reduced. Scarring is also reduced and may actually be eliminated. Nerve regrowth is speeded up. Further, there is little or no scab growth because the body no longer regards the infected area as a location which must be protected.

The wound should be covered completely by the composition of the present invention throughout the first half of the healing process. Also, a portion of the area peripheral to the wound should be covered. For the remaining healing time, the wound itself should remain covered. If pain returns, full coverage should be restored.

Existing scars may be softened and reduced by application of the inventive composition.

The effective use of the present invention can be accelerated if the applied inventive composition is kept covered and moist.

The application of heat to the wound is also helpful.

Penicillin has been a widely prescribed antibiotic composition since the 1930's.

Diphenylhydramine is marketed in the United States under the name BENADRYL™.

Hydrocortisone is marketed in the United States under the name HYDROSKIN™.

The bactericide combination of neomycin/bactracine/polymyxin B sulfate is marketed in the United States under the name BACTINE™.

In some embodiments of the present invention, 10 grains of antibiotic and 10 grains of antihistamine are mixed together. To that mixture is added 6 to 12, or even more, grains of cream or ointment. If that cream or ointment is not cortisone cream, 3 or 4 grains of cortisone cream may be included. A liquid may be required at this point to achieve the proper consistency.

Injectable antihistamine and antiinflammatory preparations may be used. The addition of water or mineral oil to noninjectable antihistamine and antiinflammatory preparations is also effective in making paste of a workable consistency.

The present invention is further described by the following examples which should not be construed as limiting the scope of the invention in any respect.

EXAMPLE I

The powder from twelve 500 mg. penicillin tablets was combined with two 50 mg. ampules of injectable Benadryl™. Added thereto was about a 2-½" to 3" squirt of Rugby Hydroskin™ and a few drops of Bactine™ until the mixture was thinner than honey.

This composition was then rubbed into a clean scalp at night and removed each morning for eight days. Within eight weeks hair growth was observed.

EXAMPLE II

A patient suffered a fungus infection under his toenails which had ridged them up to a considerable extent. On a clean toenail three applications of the composition of Example I brought back the pink skin under the nail. All of the white was gone.

EXAMPLE III

To a patient suffering from scar tissue behind his ear was subjected to repeated applications of the composition of Example I. Over an extended period of about three months, all of the scar tissue but one wrinkle and all of the effected flesh but one dot were gone.

What I claim is:

1. A method of treating a problem or disorder of the nervous system in a human patient, comprising the step of applying to the skin of the patient a pharmaceutical composition in the form of a topical application comprising (A) as an effective ingredient, a mixture comprising
      (1) an antibiotic medication;
      (2) an antihistamine; and
   (B) a physiologically acceptable carrier,
      wherein said antibiotic and said antihistamine are present in relative amounts of 30:70 to 70:30% by weight.

2. The method of claim 1, wherein the antiinflammatory medication is hydrocortisone cream.

3. The method of claim 1, wherein the mixture further comprises an antiinflammatory medication.

4. The method of claim 1, wherein the mixture further comprises a bactericide combination of neomycin/bactracine/polymyxin B sulfate.

5. The method of claim 1, wherein the antihistamine is bromopheniramine.

6. The method of claim 1, wherein the antihistamine is chlorpromazine.

7. The method of claim 1, wherein the antihistamine is diphenylhydramine hydrochloride.

8. A method of imparting an anaesthetisizing effect to a patient, comprising the step of applying to the skin of the patient a pharmaceutical composition in the form of a topical application comprising (A) as an effective ingredient, a mixture comprising
      (1) an antibiotic medication;
      (2) an antihistamine; and
   (B) a physiologically acceptable carrier,
      wherein said antibiotic and said antihistamine are present in relative amounts of 30:70 to 70:30% by weight.

9. The method of claim 8, wherein the antiinflammatory medication is hydrocortisone cream.

10. The method of claim 8, wherein the mixture further comprises an antiinflammatory medication.

11. The method of claim 8, wherein the mixture further comprises a bactericide combination of neomycin/bactracine/polymyxin B sulfate.

12. The method of claim 8, wherein the antihistamine is bromopheniramine.

13. The method of claim 8, wherein the antihistamine is chlorpromazine.

14. The method of claim 8, wherein the antihistamine is diphenylhydramine hydrochloride.

* * * * *